United States Patent [19]

Hirota

[11] Patent Number: 4,923,862

[45] Date of Patent: May 8, 1990

[54] TOPICAL PREPARATION CONTAINING OFLOXACIN

[75] Inventor: Sadao Hirota, Tokyo, Japan

[73] Assignee: Daiichi Seiyaku Co., Ltd., Tokyo, Japan

[21] Appl. No.: 133,975

[22] Filed: Dec. 17, 1987

[30] Foreign Application Priority Data

Dec. 18, 1986 [JP] Japan ................................. 61-302412

[51] Int. Cl.$^5$ ........................................... A61K 31/535
[52] U.S. Cl. .................................. 514/230.2
[58] Field of Search ......................................... 514/233

[56] References Cited

U.S. PATENT DOCUMENTS 4,382,892  5/1983  Hayakawa .......................... 548/950

FOREIGN PATENT DOCUMENTS 0142426  5/1985  European Pat. Off. ............ 514/233

OTHER PUBLICATIONS

Chemical Abstracts, vol. 104, No. 15, p. 382, Abstract No. 126370e (Apr. 14, 1986).

Primary Examiner—Jerome D. Goldberg
Attorney, Agent, or Firm—Sughrue, Mion, Zinn, Macpeak & Seas

[57] ABSTRACT

A topical preparation containing, as an active ingredient, 9-fluoro-3-methyl-10-(4-methyl-1-piperazinyl)-7-oxo-2,3-dihydro-7H-pyrido[1,2,3][1,4]-benzoxazine-6-carboxylic acid or a salt thereof.

4 Claims, No Drawings

TOPICAL PREPARATION CONTAINING OFLOXACIN

FIELD OF THE INVENTION

This invention relates to an antimicrobial topical preparation containing Ofloxacin as an active ingredient.

BACKGROUND OF THE INVENTION

Ofloxacin [i.e., (±)-9-fluoro-3-methyl-10-(4-methyl-1-piperazinyl)-7-oxo-2,3-dihydro-7H-pyrido[1,2,-3de][1,4]benzoxazine-6-carboxylic acid] is an excellent antimicrobial agent as disclosed in U.S. Pat. No. 4,382,892 and has been chiefly administered as an oral preparation as described, e.g., Japanese Patent Application (OPI) No. 46986/82 (the term "OPI" as used herein means "unexamined published Japanese patent application"). In particular, one of the optical isomers of Ofloxacin, S-(-)-9-fluoro-3-methyl-10-(4-methyl-1-piperazinyl)-7-oxo-2,3-dihydro-7H-pyrido[1,2,3de][1,4-]benzoxazine-6-carboxylic acid (hereinafter referred to as S-compound) described in U.S. patent application Ser. No. 876,623 filed June 20, 1986, exhibits potential antimicrobial activities and is expected for use as various pharmaceuticals as reported in *Antimicrobial Agent & Chemotherapy*, Vol. 29, 163-164 (1986)

SUMMARY OF THE INVENTION

As a result of extensive investigations, it has now been found that Ofloxacin or its optical isomer can be utilized as topical preparations and, thus, reached the present invention.

This invention relates to a topical preparation containing, as an active ingredient, 9-fluoro-3-methyl-10-(4-methyl-1-piperazinyl)-7-oxo-2,3-dihydro-7H-pyrido[1,2,3-de][1,4]benzoxazine-6-carboxylic acid or an S-isomer thereof, or a salt thereof.

DETAILED DESCRIPTION OF THE INVENTION

The term "salt" as used herein for the active ingredient means a pharmaceutically acceptable salt and includes, for example, a hydrochloride, an acetate, a lactate, a citrate, a sulfate, a nitrate, a tartarate, a sodium salt, a potassium salt, an ammonium salt and the like. These salts can be used in an equimolar amount to the free compound.

A variety of dose forms and bases can be applied to the topical preparations according to the present invention. Hydrogels and creams are superior in absorbability and, in particular, hydrogels using carboxymethyl cellulose (CMC) as a base and creams of an oil-in-water (O/W) type are particularly preferred. General ointments using vaseline, bases for hydrophilic ointments, bases for absorption ointments, or Macrogol bases sometimes show low percutaneous absorption, while S-compound may be advantageous in such cases. Percutaneous absorption is not always required as in some preparations such as ophthalmic ointments.

The present invention will be described by referring to typical formulation examples.

(1) Sodium CMC Hydrogel

| (1) Sodium CMC Hydrogel | |
| --- | --- |
| (a) Ofloxacin | 1 to 50 mg |
| (in case of S-compound) | (0.5 to 25 mg) |
| (b) Sodium CMC | 10 to 100 mg |
| (c) Polyhydric alcohol | 50 to 500 mg |
| (d) Acid | 0.25 to 0.28 mg per mg of Ofloxacin |
| (e) Sodium hydroxide | 0.10 to 0.12 mg per mg of Ofloxaxin |
| (f) Antiseptic | 0.1 to 1.0 mg |
| (g) Water | to make 1 g |

Sodium CMC which can be used suitably has a molecular weight of from 10,000 to 500,000 and a degree of etherification of from 0.3 to 3.0. The acid to be used includes hydrochloric acid, lactic acid, citric acid, acetic acid, tartaric acid, etc.

The polyhydric alcohol which is suitable for general use includes glycerin, propylene glycol, 1,3-butylene glycol, sorbitol, etc.

The antiseptic to be used can be selected from those commonly employed for topical preparations. Specific examples of usable antiseptics include a methyl, ethyl, propyl, or butyl ester of p-hydroxybenzoic acid or a mixture thereof, 4-chloro-m-cresol, etc.

The hydrogel can be prepared by dissolving Ofloxacin or S-compound in the ingredients (a), (d), and (e), and a part of the ingredient (g) to prepare a solution in high concentrations and uniformly mixing the solution with a hydrogel separately prepared from the ingredients (b), (c), and (f), and the rest of the ingredient (g). The above-described order of addition of the ingredients is not limitative.

(2) Creams (O/W Emulsion)

| (2) Creams (O/W Emulsion) | |
| --- | --- |
| (a) Ofloxacin | 1 to 50 mg |
| (in case of S-compound) | 0.5 to 25 mg |
| (b) Fats and oils | 100 to 500 mg |
| (c) Polyhydric alcohol | 50 to 500 mg |
| (d) Emulsifier | 10 to 50 mg |
| (e) Acid | 0.25 to 0.28 mg per mg of Ofloxacin |
| (f) Sodium hydroxide | 0.10 to 0.11 mg per mg of Ofloxacin |
| (g) Antiseptic | 0.1 to 1.0 mg |
| (h) Water | to make 1 g |

The fats and oils to be used include higher hydrocarbons, e.g., liquid paraffin, vaseline, squalane, etc.; higher alcohols, e.g., cetyl alcohol, stearyl alcohol, etc.; higher esters, e.g., tristearyl glyceride, tripalmityl glyceride, distearyl glyceride, monostearyl glyceride, cholesteryl stearate, isopropyl myristate, etc.; and waxes, e.g., beeswax, Japan wax, etc.

The emulsifier to be used includes nonionic surface active agents, such as polyoxyethylene derivatives of fats and oils, e.g., Tween series (products of Atlas Powder Corp.), MYRJ series (products of Atlas Powder Corp., I.C.I. America, i.e., polyethylene laurate, polyethylene myristate, polyethylene palmitate, polyethylene stearate, polyethylene oleate, etc.), BRIJ series (products of Atlas Powder Corp., I.C.I. America, i.e., polyethylene lauryl ether, polyethylene myristyl ether, polyethylene oleyl ether, etc.), polyoxyethylene castor oil derivatives, etc., Pluronic series (product of Wyandotte Chemicals), polyglycerin esters or ether of fats and oils, sugar esters, e.g., monofatty acid sucrose esters, etc.; amphoteric surface active agents, e.g., lecithin, etc.; and the like.

The antiseptic to be used is selected from those enumerated in Formulation (1). The kinds and amounts of the polyhydric alcohol and acid are in accordance with Formulation (1).

The creams can be obtained by preparing a high concentration solution of Ofloxacin or S-compound from the ingredients (a), (c), and (e) to (h), adding a molten solution of fats and oils prepared by mixing the ingredients (b) and (d) under heating to the solution of Ofloxacin or S-compound while stirring to form a W/O emulsion, and cooling the emulsion to cause phase transition to form an O/W emulsion. The above-described order of adding the ingredients is not limitative. The Ofloxacin or S-compound as active ingredient may be in the form of its salt.

In some cases, S-compound is more advantageous than Ofloxacin because of its high antimicrobial activities and high water solubility. In addition, when a 0.5% (wt./vol.) aqueous solution of S-compound was preserved at a pH of from 3 to 10 for 2 weeks, and the residual amount of S-compound was determined, no decomposition was observed at all, indicating extremely high stability of S-compound.

The present invention will now be illustrated in greater detail by way of Examples and Test Example, but it should be understood that the present invention is not construed to be limited thereto.

EXAMPLE 1 preparation of Sodium CMC Hydrogel

In a beaker were put 200 ml of concentrated glycerin and 50 ml of 1,3-butylene glycol, and 0.6 g of ethyl p-hydroxybenzoate and 0.4 g of propyl p-hydroxybenzoate were added thereto, followed by heating at 60° C. to form a solution. To the solution was added 25 g of sodium CMC ("CMC Disel 2200H" produced by Disel Ltd.), and the content was thoroughly and uniformly dispersed in a vacuum homomixer. After 10 minutes, the atmosphere was evacuated to a pressure of 380 mmHg for deaeration.

In a separate beaker was placed 600 ml of purified water, and 2.65 g of lactic acid was dissolved therein. An aqueous solution of 1.1 g of sodium hydroxide in 50 ml of water was added to the lactic acid aqueous solution. The resulting solution was found to have a pH of 5.85±0.1. In case where the pH was out of this range, the pH of the solution was adjusted so as to fall within this range with a sodium hydroxide aqueous solution or a hydrochloric acid aqueous solution.

In the thus prepared lactic acid buffer solution (pH=5.85) was dissolved 10 g of Ofloxacin or 5 g of S-compound. The resulting solution was poured all at once into the sodium CMC dispersion in the vacuum homomixer at 40° C. under normal pressure while stirring, and purified water was added thereto to make 1 Kg. The mixture was stirred at 40° C. and 380 mmHg for 10 minutes to complete gelation. After the pressure was elevated up to 760 mmHg, the mixture was heated at 80° C. for 30 minutes for sterilization and cooled to room temperature, and filled in a tube.

EXAMPLE 2

Preparation of Cream (1) In a beaker were placed 90 g of squarane, 30 g of cetanol, 20 g of stearyl alcohol, 50 g of monostearyl glyceride, and 10 g of polyoxyethylene (7 mol) cetyl ether ("Nikkol BC-7" produced by Nikko Chemical Co., Ltd.), and the mixture was melted at 75° C.

(2) In a separate beaker were placed 50 g of 1,3-butylene glycol, 0.3 g of ethyl p-hydroxybenzoate, 0.2 g of propyl p-hydroxybenzoate, and 40 g of polyoxyethylene (20 mols) cetyl ether, and the mixture was heated at 70° C. to form a solution.

(3) In 500 ml of purified water were dissolved 1.2 g of lactic acid and 0.5 g of sodium hydroxide, and 50 ml of a 65 wt % D-sorbitol aqueous solution was added thereto to prepare a lactic acid buffer solution. The solution was combined with the solution prepared in (2) above.

(4) Ten grams of Ofloxacin or 5 g of S-compound was dissolved in the solution prepared in (3) above, and the solution was adjusted to a pH of 5.0 to 5.5 by addition of a 0.1N sodium hydroxide aqueous solution or a 0.1N hydrochloric acid aqueous solution.

(5) The resulting solution was maintained at 80° C. for 30 minutes for sterilization.

(6) The aqueous solution prepared in (5) above was poured into the molten solution prepared in (1) above while stirring to obtain a W/O emulsion.

(7) The resulting emulsion was cooled to 40° C. while vigorously stirring in a vacuum homomixer at 6,000 rpm. During the cooling, the emulsion underwent phase transition from W/O to O/W. A trace amount of a flavoring agent was added to the cream at 40° C., and purified water was added thereto to make 1 Kg, followed by gently stirring at 40° C. and 380 mmHg for 10 minutes to homogenize. After the pressure was returned to normal pressure, the cream was filled in a tube.

EXAMPLE 3

Preparation of Vaseline Ointment

S-Compound: 5 g
(in case of Ofloxacin): 10 g
White petrolatum (J.P.): 950 g
Soft liquid paraffin (J.P.): to make 1000 g Five grams of S-compound under a 100 mesh sieve were ground in a mortar together with 10 g of soft liquid paraffin to form a suspension. White vaseline (950 g) was liquefied in a jacketed homomixer heated by steam circulating in the jacket, and the S-compound suspension was added thereto while stirring. The S-compound suspension sticking to the inner wall of the mortar was washed off with soft liquid paraffin, and the washing was combined with the content of the homomixer. Soft liquid paraffin was further added to the mixture to make 1000 g. The mixture was kneaded while circulating cold water through the jacket, followed by quenching. The resulting ointment was charged in previously sterilized aluminum tubes.

EXAMPLE 4

Preparation of Fatty Suppositories

| Preparation of Fatty Suppositories | |
|---|---|
| S-Compound | 5 g |
| Sorbitan fatty acid ester ("Nikkol SS10" produced by Nikko Chemical Co., Ltd.) | 1 g |
| Glycerin fatty acid ester ("Witepsol H15" produced by Dynamite Nobel Chemicals Inc.) | 994 g |
| Total | 1000 g |

Five grams of S-compound under a 100 mesh sieve were placed in a mortar warmed at 40 to 45° C., and 10 g of heat-molten Witepsol H15 and 1 g of Nikkol SS10 were added thereto, followed by kneading to form a suspension. Separately, 960 g of Witepsol H15 was melted and liquefied in a jacketed homomixer warmed at 40° C. by circulating warm water through the jacket, and the molten suspension in the mortar was mixed with the molten liquid in the homomixer. The suspension sticking to the inner wall of the mortar was washed with 24 g of molten Witepsol H15 and combined with the mixture in the homomixer. The molten suspension in the homomixer was charged in plastic containers for suppositories, allowed to cool to solidify. The tail end of the container was then heat-sealed.

TEST EXAMPLE

Wister male rats under ether anesthesia (body weight: 200 to 300 g; 5 rats per group) were tied out, lying on their back, and the hair was clipped over the abdomen with an electrical shaver. One gram of each of the topical preparations obtained in Examples 1 to 3 (Ofloxacin content: 10 mg) was spread on a polyethylene film (4×4 cm) to a size of 2.5×2.5 cm and attached onto the central part of the abdomen from which the hair had been completely removed, and the film was fixed thereto with an adhesive tape.

After 1, 2, 4, or 8 hours, about 0.8 ml of blood was taken from the carotid artery. The serum was separated from the blood sample, and the concentration of Ofloxacin was determined. Further, urine voided in 8 hours and the urine in the bladder after 8 hours were collected, and the Ofloxacin excretion (recovery) in urine was determined.

After the topical preparation remaining on the skin was thoroughly wiped off with a cotton swab, the entire skin to which the topical preparation had been applied was collected, homogenized, and extracted with chloroform to obtain a recovery of Ofloxacin.

These quantitative determinations were carried out by high performance liquid chromatography using 635 Model manufactured by Hitachi, Ltd. under the following conditions:

Column: Nucleosil $5C_{18}$ (or $10C_{18}$); 150×4 mm
Mobile Phase: Consisting of 150 ml of acetonitrile, 50 ml of acetic acid, and water to make 1 l.
Flow Rate: 1.0 ml/min
Detection: Fluorescence 295 nm (excitation), 470 nm (emission); UV 295 nm The results of determinations are shown in Table 1 below. Table 1 also shows the area under the curve of concentrations in serum (AUC), the time required to reach the maximum concentration in serum (T-MAX), and the reached maximum concentration in serum (C-MAX).

TABLE 1

|  | CMC Gel | Cream | Vaseline Ointment |
|---|---|---|---|
| Concentration (μg/ml) in Serum After |  |  |  |
| 1 Hour | 0.144 | 0.102 | 0.002 |
| 2 Hours | 0.262 | 0.196 | 0.000 |
| 4 Hours | 0.340 | 0.144 | 0.008 |
| 8 Hours | 0.316 | 0.164 | 0.008 |
| AUC (μg · hr · ml) | 2.190 | 1.158 | 0.042 |
| T-MAX (hr) | 6.400 | 4.000 | 3.600 |
| C-MAX (μg/ml) | 0.376 | 0.222 | 0.012 |
| Recovery in Urine (%) | 3.938 | 1.766 | 0.112 |

TABLE 1-continued

|  | CMC Gel | Cream | Vaseline Ointment |
|---|---|---|---|
| Recovery in Skin (%) | 0.742 | 0.756 | 0.432 |

It can be seen from Table 1, that gels are superior to creams, and creams are superior to vaseline ointments in terms of percutaneous absorption.

The topical preparations according to the present invention exhibit potential antimicrobial activities on staphylococcus, *Streptococcus pyogenes*, *Streptococcus haemolyticus*, enterococci, *Diprococcus pneumoniae*, *Escherichia coli*, gonococcus, microorganisms belonging to the genus Citrobacter and Shiegella, *Klabsiella pneumoniae*, microorganisms belong to the genus Enterobacter, Serratia, and Proteus, *Pseudomonas aeruginosa*, *Heomophylus influenzae*, microorganisms belonging to the genus Acinetobacter and Campylobacter, etc. and are expected to produce excellent therapeutic effects on skin diseases caused by these microorganisms. For example, the topical preparations are useful for the treatment of folliculitis, furuncle, furunculosis, carbuncle, erysipelas, panaritium, melitagra, subcutaneous abscess, hidradenitis, acne, infective atheroma, circumanal abscess, and secondary infectious diseases after injuries, operations or scalds. They are also useful for treating and preventing infection in nasal cavity or auricular cavity. Eye ointments are useful for the treatment of infectious diseases of eyes, and the like.

The topical preparations of the present invention can be administered by directly applying an appropriate amount to the affected part, or spread on sterilized gauze and attached to the skin. Eye ointments are applied to eyes, and suppositories are inserted in the anus, the vagina, etc.

The dose level is not particularly limited and ranges from 0.5 to 50 mg/cm$^2$, and usually from 1 to 10 mg/cm$^2$, being selected depending on symptoms.

When the topical preparations of the present invention were applied to the skin, there was observed no problem on antigenicity, skin sensitinogenicity, and photo-sensibilisinogenicity.

The acute toxicity of Ofloxacin in mice is LD$_{50}$ 5450 mg/Kg, p.o. and that in rats is LD$_{50}$ 3590 mg/Kg, p.o. The acute toxicity of S-compound in mice is LD$_{50}$ 244 mg/Kg, i.v.

While the invention has been described in detail and with reference to specific embodiments thereof, it will be apparent to one skilled in the art that various changes and modifications can be made therein without departing from the spirit and scope thereof.

What is claimed is:

1. A topical hydrogel or oil-in-water type cream preparation containing, as an active ingredient, an antibacterially effective amount of 9-fluoro-3-methyl-10-(4-methyl-1-piperazinyl-7-oxo-2,3-dihydro-7H-pyrido[1,2,3-de][1,4]-benzoxazine-6-carboxylic acid or a pharmaceutically acceptable salt thereof.

2. A topical preparation as claimed in claim 1, wherein said preparation is a hydrogel.

3. A topical preparation as claimed in claim 1, wherein said preparation is an oil-in-water cream.

4. A topical preparation as claimed in claim 1, wherein said active ingredient is S-(-)-9-fluoro-3-methyl-10-(4-methyl-1-piperazinyl)-7-oxo-2,3-dihydro-7H-pyrido[1,2,3-de][1,4]benzoxazine-6-carboxylic acid or a pharmaceutically acceptable salt thereof.

* * * * *